US009036773B2

(12) United States Patent
David et al.

(10) Patent No.: US 9,036,773 B2
(45) Date of Patent: May 19, 2015

(54) METHOD FOR X-RAY PHASE CONTRAST AND DARK-FIELD IMAGING USING AN ARRANGEMENT OF GRATINGS IN PLANAR GEOMETRY

(75) Inventors: Christian David, Lauchringen (DE); Marco Stampanoni, Endingen (CH)

(73) Assignee: Paul Scherrer Institut, Villigen PSI (CH)

( * ) Notice: Subject to any disclaimer, the term of this patent is extended or adjusted under 35 U.S.C. 154(b) by 220 days.

(21) Appl. No.: 13/807,537

(22) PCT Filed: Apr. 4, 2011

(86) PCT No.: PCT/EP2011/055168
§ 371 (c)(1),
(2), (4) Date: Feb. 28, 2013

(87) PCT Pub. No.: WO2012/000694
PCT Pub. Date: Jan. 5, 2012

(65) Prior Publication Data
US 2014/0112440 A1    Apr. 24, 2014

(30) Foreign Application Priority Data

Jun. 28, 2010    (EP) .................................... 10167569

(51) Int. Cl.
*A61B 6/00* (2006.01)
*G01N 23/04* (2006.01)
(Continued)

(52) U.S. Cl.
CPC .............. *G01N 23/04* (2013.01); *A61B 6/4035* (2013.01); *A61B 6/4291* (2013.01); *A61B 6/484* (2013.01);
(Continued)

(58) Field of Classification Search
CPC .............................. A61B 6/4291; A61B 6/484

USPC .................................................. 378/36, 37, 62
See application file for complete search history.

(56) References Cited

U.S. PATENT DOCUMENTS 3,988,589 A * 10/1976 Leask ............................ 378/149
5,812,629 A *  9/1998 Clauser .......................... 378/62
(Continued)

FOREIGN PATENT DOCUMENTS

CN          101257851 A      9/2008
EP          1 731 099 A1    12/2006
(Continued)

OTHER PUBLICATIONS

W. Werner: "X-ray efficiencies of blazed gratings in extreme off-plane mountings", Applied Optics, vol. 16, No. 8, Aug. 1, 1977, pp. 2078-2080, XP55001483.
(Continued)

*Primary Examiner* — Thomas R Artman
(74) *Attorney, Agent, or Firm* — Laurence A. Greenberg; Werner H. Stemer; Ralph E. Locher

(57) ABSTRACT

An X-ray arrangement is suitable to record absorption, phase contrast, and dark field images of an object. The visibility of low absorbing specimens is improved and required radiation dose is reduced. The assembly includes an X-ray source; two or more gratings; a position-sensitive detector with spatially modulated detection sensitivity; a recorder for recording the images; an evaluator for evaluating the intensities for each pixel to identify the characteristic of the object for each individual pixel as an absorption and/or a differential phase contrast and/or an x-ray scattering dominated pixel. Images are collected by rotating from 0 to n or 2n either the sample or the assembly. The gratings are produced with planar geometry. The X-rays pass through the gratings parallel to the substrate. The grating structures extend along the X-ray path which determines the phase shift. The attenuation of the X-rays caused by the grating structures is no longer given by the thickness, but by the length of the grating structures.

20 Claims, 7 Drawing Sheets

(51) Int. Cl.
*G21K 1/02* (2006.01)
*G21K 1/06* (2006.01)

(52) U.S. Cl.
CPC ............... *A61B 6/502* (2013.01); *G21K 1/025* (2013.01); *G21K 1/06* (2013.01); *G21K 2201/067* (2013.01); *G21K 2207/005* (2013.01)

(56) References Cited

U.S. PATENT DOCUMENTS

| | | | | |
|---|---|---|---|---|
| 6,363,136 | B1* | 3/2002 | Flisikowski et al. | 378/154 |
| 7,180,982 | B2* | 2/2007 | Schneider et al. | 378/154 |
| 7,362,849 | B2* | 4/2008 | Short et al. | 378/154 |
| 7,639,786 | B2* | 12/2009 | Baumann et al. | 378/145 |
| 7,889,838 | B2* | 2/2011 | David et al. | 378/36 |
| 8,139,711 | B2* | 3/2012 | Takahashi | 378/36 |
| 8,532,252 | B2* | 9/2013 | Nakamura | 378/36 |
| 8,718,228 | B2* | 5/2014 | Nakamura et al. | 378/36 |
| 8,767,915 | B2* | 7/2014 | Stutman et al. | 378/62 |
| 2006/0002512 | A1* | 1/2006 | Cho et al. | 378/84 |
| 2007/0183579 | A1 | 8/2007 | Baumann et al. | |
| 2007/0183581 | A1 | 8/2007 | Heismann et al. | |
| 2007/0183583 | A1 | 8/2007 | Baumann et al. | |
| 2009/0092227 | A1* | 4/2009 | David et al. | 378/36 |
| 2009/0316857 | A1 | 12/2009 | David et al. | |
| 2009/0323899 | A1* | 12/2009 | Dorscheid et al. | 378/154 |
| 2010/0061508 | A1* | 3/2010 | Takahashi | 378/36 |
| 2010/0074395 | A1* | 3/2010 | Popescu | 378/16 |
| 2010/0327175 | A1 | 12/2010 | Nesterets et al. | |
| 2011/0013743 | A1 | 1/2011 | Nakamura et al. | |
| 2012/0020461 | A1* | 1/2012 | Roessl et al. | 378/87 |
| 2013/0279659 | A1* | 10/2013 | Stampanoni et al. | 378/62 |
| 2014/0112440 | A1* | 4/2014 | David et al. | 378/62 |

FOREIGN PATENT DOCUMENTS

| | | |
|---|---|---|
| EP | 1 879 020 A1 | 1/2008 |
| JP | 2006259264 A | 9/2006 |
| WO | 2009/076700 A1 | 6/2009 |
| WO | 2009/113726 A2 | 9/2009 |

OTHER PUBLICATIONS

Heilmann: "Reflection Grating Development Update", , Nov. 19, 2003, XP55001533, Retrieved from the Internet: URL:http://snl.mit.edu/papers/presentations/2003/Heilmann/RKH-Con-X-FST-11-19-2003.pdf [retrieved on Jun. 28, 2011].

Jergel M et al: "Multilayer gratings for X-UV optics", Acta Physica Slovaca, Veda, Bratislava, CZ, vol. 50, No. 4, Aug. 1, 2000 , pp. 427-438, XP008138492, ISSN: 0323-0465.

Leonid I. Goray: "Off-plane grazing-incidence fan-groove blazed grating to serve as high-efficiency spectral purity filter for EUV lithography", SPIE, PO Box 10 Bellingham WA 98227-0010 USA, vol. 6317, 2006, XP040228992.

Webster Cash, Ann Shipley: "Off-plane grating mount tolerances for Constellation-X", SPIE, PO Box 10 Bellingham WA 98227-0010 USA, vol. 5488, 2004, pp. 335-340, XP040187996.

Ann Shipley, Randall McEntaffer: "Thin substrate grating array for sounding rocket and satellite payloads", SPIE, PO Box 10 Bellingham WA 98227-0010 USA, vol. 7011, 2008, pp. 70112I-1-70112I-10, XP040439536.

C David et al: "Fabrication of diffraction gratings for hard X-ray phase contrast imaging", Microelectronic Engineering, vol. 84, No. 5-8, May 1, 2007, pp. 1172-1177, XP55001531, ISSN: 0167-9317.

Bech M et al: "Advanced contrast modalities for X-ray radiology: Phase-contrast and dark-field imaging using a grating interferometer", Zeitschrift Fuer Medizinische Physik, Urban Und Fischer, Jena, DE, vol. 20, No. 1, Mar. 1, 2010, pp. 7-16, XP026967197, ISSN: 0939-3889 [retrieved on Jan. 15, 2010].

* cited by examiner

A)

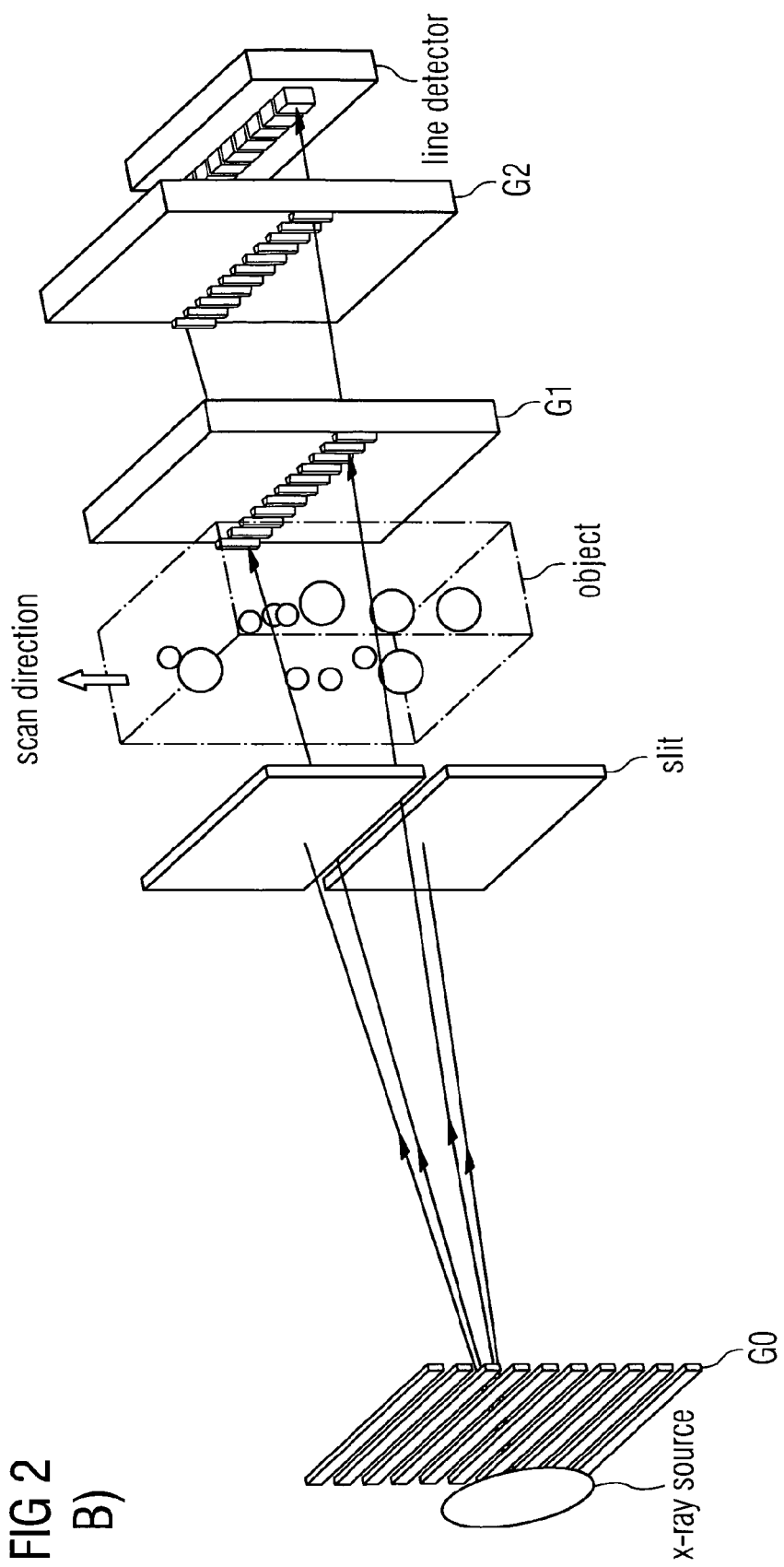

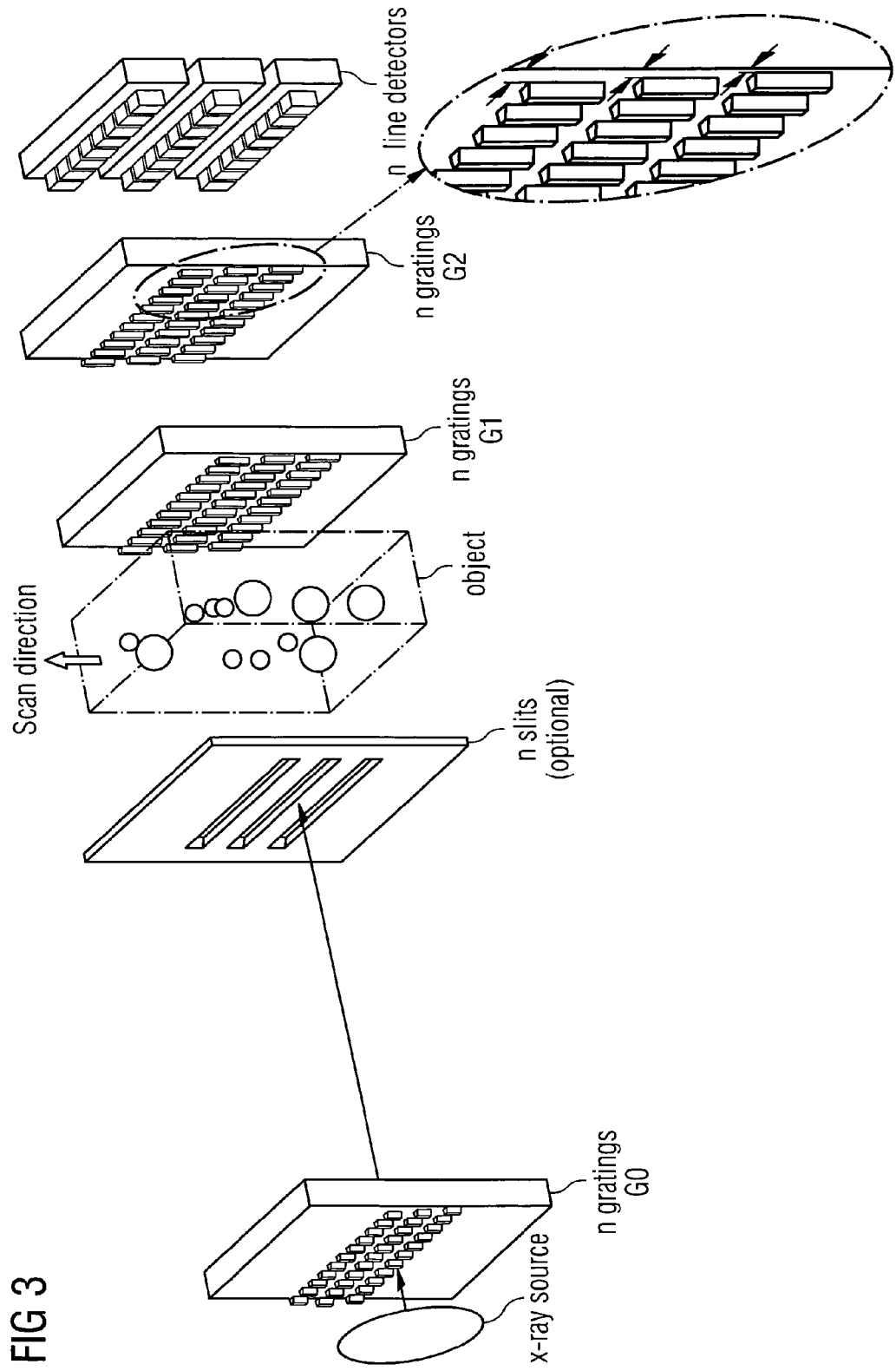

high aspect ratio gratings detector

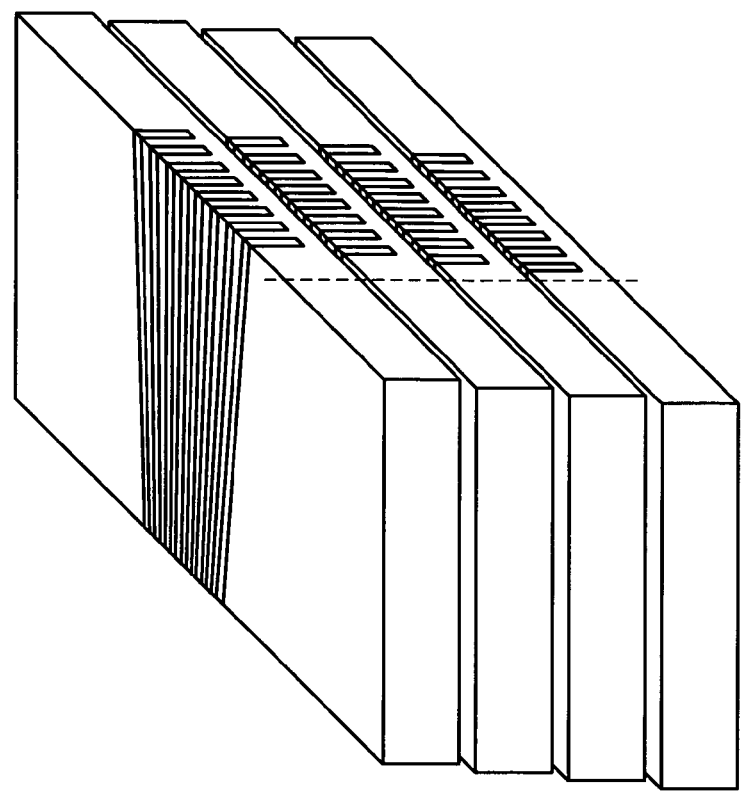
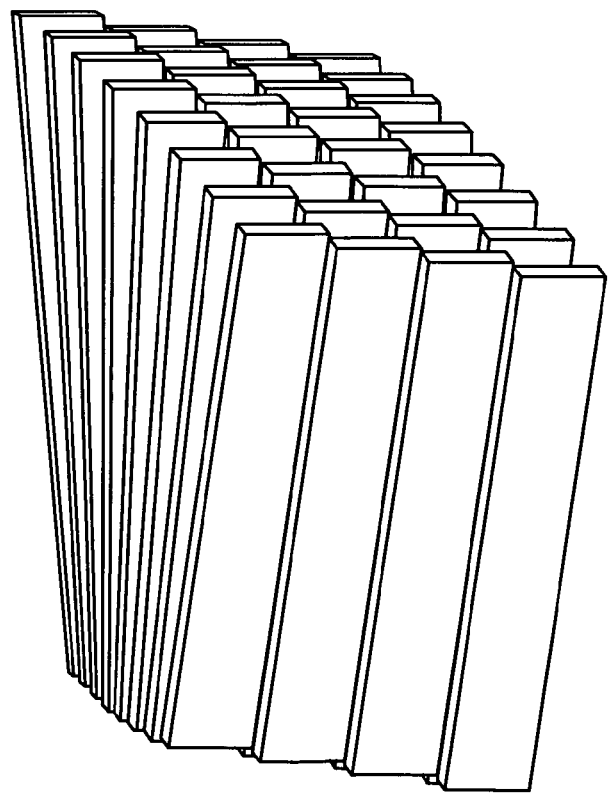
FIG 6

METHOD FOR X-RAY PHASE CONTRAST AND DARK-FIELD IMAGING USING AN ARRANGEMENT OF GRATINGS IN PLANAR GEOMETRY

BACKGROUND OF THE INVENTION

1. Field of the Invention

The present invention is a variation of a set-up to generate phase contrast X-ray images using special arrangements of gratings. The set-up can be used to record absorption contrast images, phase contrast images, and dark field contrast images of an object. The arrangement thereby improves the visibility of low absorbing specimens and can therefore significantly reduce the required radiation dose without compromising the image quality or provide complimentary image information.

In comparison to existing arrangements in x-ray grating-based imaging systems, the present configuration uses gratings made in a novel planar geometry. This approach has two essential advantages:
 (i) it allows for the fabrication of gratings with extreme aspect ratios, making the method particularly useful for high x-ray energies; and
 (ii) it can be used to realize grating geometries matched to divergent beam geometries. This arrangement of gratings is particularly suited for a scanning type of x-ray phase contrast imaging, comprising one or several line detectors and a translation of the sample during image acquisition.

Envisaged applications are for medical scanners (in particular mammography), inspection at industrial production lines, non-destructive testing, and homeland security.

2. Physical Background

It is well known that, differently from conventional visible light optics, the refractive index in X-ray optics is very close to and smaller than unity. In first approximation, for small and negligible anisotropy in the medium, the index of refraction characterizing the optical properties of a tissue can be expressed—including X-ray absorption—with its complex form: $n = 1 - \delta - i\beta$ where $\delta$ is the decrement of the real part of the refractive index, characterizing the phase shifting property, while the imaginary part $\beta$ describes the absorption property of the sample. In conventional absorption-based radiography, the X-ray phase shift information is usually not directly utilized for image reconstruction. However, at photon energies greater than 10 keV and for light materials (made up of low-Z elements), the phase shift term plays a more prominent role than the attenuation term because $\beta$ is typically three orders of magnitude larger than $\beta$. As a consequence, phase-contrast modalities can generate significantly greater image contrast compared to conventional, absorption-based imaging. Furthermore, far from absorption edges, $\delta$ is inversely proportional to the square of the X-ray energy whilst $\beta$ decreases as the fourth power of energy. A significant consequence of this mechanism is that phase signals can be obtained with much lower dose deposition than absorption, a very important issue when radiation damage has to be taken into account such as in biological samples or in living systems.

Several approaches have been developed in order to record the phase signal. They can be classified as interferometric methods (with crystals), phase propagation methods, techniques based on an analyzer crystal, or on x-ray gratings. The described invention is in context with the latter technique.

Grating based x-ray imaging setups essentially detect the deflections of x-rays in the object. Such deflections can be either caused by refraction on phase shift gradients in the object resulting in differential phase contrast (DPC) or by scattering on inhomogeneities in the sample resulting in the so-called dark-field image (DFI) contrast. The DPC image signal can be used to obtain phase contrast (PC) images by image processing routines.

Set-ups with two gratings (G1 and G2) or three gratings (G0, G1, and G2) can be applied to record the deflection of the x-rays. In the case of a two-grating set-up, the source needs to fulfill certain requirements regarding its spatial coherence, while in a three grating setup no spatial coherence is required. Therefore, the three grating set-up is suited for use with incoherent x-ray sources, in particular with x-ray tubes.

To separate the conventional attenuation contrast (AC) from the DPC and DFI contrast, a phase-stepping approach is applied. One of the gratings is displaced transversely to the incident beam whilst acquiring multiple images. The intensity signal at each pixel in the detector plane oscillates as a function of the displacement. The average value of the oscillation represents the (AC). The phase of the oscillation can be directly linked to the wave-front phase profile and thus to the DPC signal. The amplitude of the oscillation depends on the scattering of x-rays in the object and thus yields the DFI signal.

For the (two or three) gratings, several approaches have been proposed and applied. The grating G0 (if required) is the one closest to the source. It usually consists of a transmission grating of absorbing lines with the period p0. It can be replaced by a source that emits radiation only from lines with the same period. The grating G1 is placed further downstream of the source. It consists of lines with a period p1. The grating G2 is the one most downstream of the setup. It usually consists of a transmission grating of absorbing lines with the period p2. It can be replaced by a detector system that has a grating-like sensitivity with the same period.

Two regimes of setups can be distinguished: in the so called "near field regime" and the "Talbot regime". In the "near field regime", the grating periods p, grating distances d and the x-ray wavelength $\lambda$ are chosen such, that diffraction effects are negligible. In this case, all gratings need to consist of absorbing lines. In the "Talbot regime", diffraction on the grating structures is significant. Here G1 should consist of grating lines that are either absorbing or, preferentially, phase shifting. Several amounts of phase shift are possible, preferentially $\pi/2$ or multiples thereof. The grating periods must be matched to the relative distances between the gratings. In case of setups in the "Talbot regime" the Talbot effect needs to be taken into account to obtain good contrast.

The sample is mostly placed between G0 of G1 (or upstream of G1 in case of a two-grating set-up), however it can be advantageous to place it between G1 and G2. The presented inventions are relevant in all of the abovementioned cases, i.e. in the two- and three-grating case, in the case of the "nearfield regime" and the "Talbot regime", and for the sample placed upstream or downstream of G1.

Some commercial x-ray imaging systems use a scanning scheme for imaging. The sample is irradiated with a fan beam, and a line detector and a sample translation are used to acquire a 2-dimensional image of the object. The main advantages of the scheme are, that line detectors are much less expensive than 2D detectors, and that they can be made with higher efficiency, which reduces radiation dose to the sample.

A combination of grating-based x-ray imaging with a scanning setup has been proposed, and experimentally verified (see FIG. 2). This scanning set-up is of particular interest in context of the invention described further below. When a single set of gratings and line detector is used, either the single step approach can be applied, or a phase stepping needs to be done by moving one of the three gratings perpendicular to the grating lines. This phase stepping scan needs to be nested with the object scan, and can thus be very complicated or time consuming. A nested phase stepping and object scan can be avoided by using n fan beams, n sets of grating and n line-detectors. By aligning each of the n sets with a different phase-stepping position, the object will be scanned in n phase-step positions without moving any mechanical parts (besides the object).

The key components of grating-based x-ray imaging are obviously the gratings. Two main technical difficulties are encountered in the fabrication and application of these gratings:

1) The sensitivity of grating based imaging becomes better with decreasing grating periods, which are therefore in the micrometer range (typ. 1-20 microns). On the other hand, the required thickness of the grating lines (i.e. their dimension along the beam path) has to be sufficient to induce enough attenuation (in case of absorbing lines) or sufficient phase shift (in case of phase-shifting gratings). Especially for high x-ray energies, for example above 50 keV, the required grating line thicknesses are usually much higher than the period of the grating lines, resulting in very high aspect ratios. For high x-ray energies, gratings with such high aspect ratios are very difficult, or even impossible, to fabricate.

2) For the use with x-ray tube sources, the image detector size is comparable to the source distance, meaning that the beam has a significant divergence, resulting in a cone-beam geometry, where a 2-dimensional detector is used, and in a fan-beam geometry, where a 1-dimensional (line) detector is used. When the gratings are made on flat substrates with the surface normal along the optical axis (as indicated in FIG. 1), the beams towards the edge of the image field will hit the grating angle in an inclined angle as indicated in FIG. 4. This leads to loss of phase or dark-field contrast, and poses a fundamental problem especially at high x-ray energies where extreme aspect ratios of the grating lines are required. The grating lines would need to be tilted towards the source point, which is difficult to realize for substrates oriented normal to the optical axes. Attempts to bend the substrate or to compose the gratings of smaller pieces, each facing towards the source, have been proposed. However these approaches are technically difficult and expensive.

BRIEF SUMMARY OF THE INVENTION

The present invention now has the objective to:
1. Allow to fabricate extremely high aspect ratios gratings for high x-ray energies
2. Allow to shape such gratings to arbitrary geometries, in particular to match fan-beam geometries.
3. Allow to place the gratings in such a manner that phase-stepping can be performed without moving any component other than the sample These objectives are achieved according to the present inventions by an arrangement for x-rays, in particular hard x-rays, for obtaining quantitative x-ray images from a sample including:
a) an X-ray source (x-ray);
b) a set of at least two gratings (G0, G1 and G2 and G1, G2 resp.);
c) a position-sensitive detector (PSD) with spatially modulated detection sensitivity having a number of individual pixels;
d) means for recording the images of the detector (PSD);
e) means for evaluating the intensities for each pixel in a series of images in order to identify the characteristic of the object for each individual pixel as an absorption dominated pixel and/or a differential phase contrast dominated pixel and/or an x-ray scattering dominated pixel;
f) wherein the series of images is collected by continuously or stepwise rotating from 0 to $\pi$ or $2\pi$ either the sample or the arrangement and the source relative to the sample
g) wherein the gratings (G0 (if required), G1 and G2) or part of such a grating set are manufactured according to a novel planar geometry where the X-rays pass through the gratings parallel to the substrate,
h) whereby the grating structures extend along the x-ray path which determines the phase shift and attenuation that these grating structures cause to the x-rays, being no longer given by the thickness of the structures, but by the length of the grating structures.

Further preferred examples of the present invention are listed in the dependent claims.

The present invention is hereinafter described. The attached drawing are helping to understand the scope and the preferred embodiments of the present invention.

BRIEF DESCRIPTION OF THE SEVERAL VIEWS OF THE DRAWING

FIG. 3 illustrates an X-ray scanning setup using n fan beams, n grating sets and n line detector sets. n=3 is shown here for simplicity. By aligning each of the n sets with a different phase-stepping position, a mechanical phase stepping can be avoided. Here, the three G2 gratings are offset with respect to each other to achieve this difference in phase-stepping position (see enlarged sketch of the region within the dashed circle).

FIG. 6 is a schematic illustration on how to avoid mechanical phase stepping by using several gratings with appropriate alignment.

DESCRIPTION OF THE INVENTION

Figure 1:
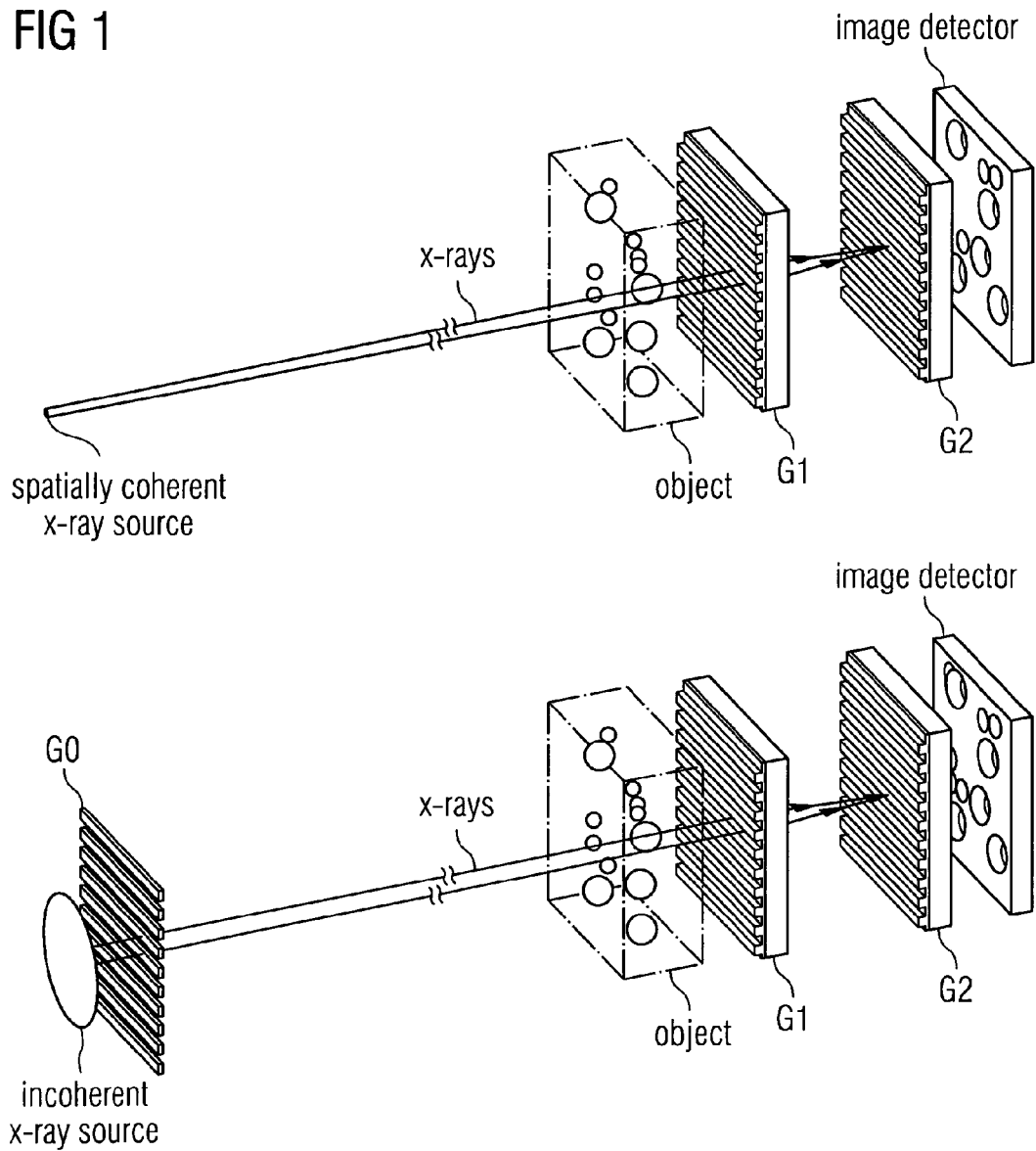
FIG. 1 is a two-grating set-up (top) and three-grating set-up (bottom) for x-ray imaging.
Figure 2:
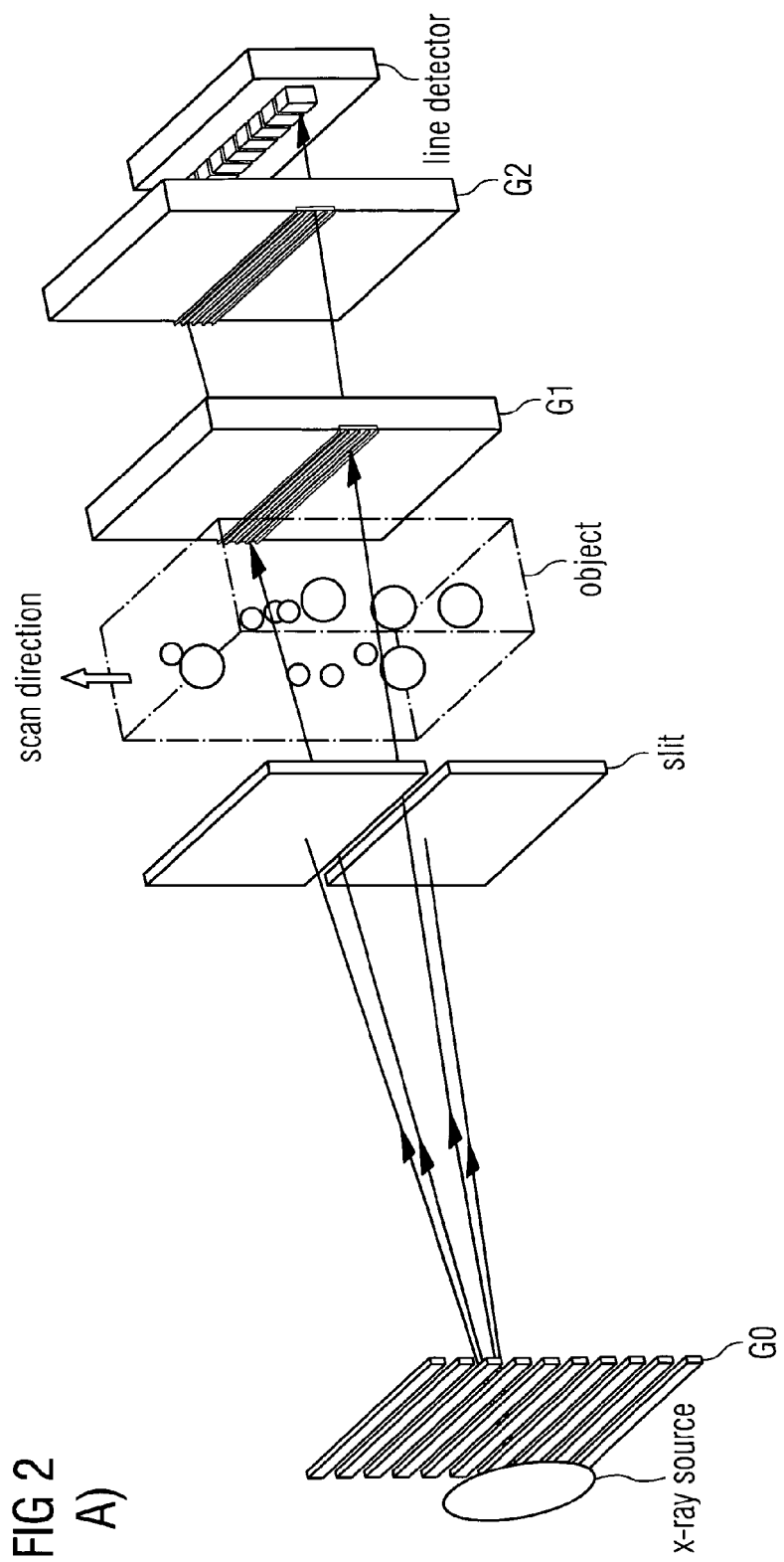
FIG. 2 shows an X-ray scanning set-up comprising a line detector. The sample is imaged by scanning it through the fan beam. Two orientations of the grating lines are possible.
Figure 4:
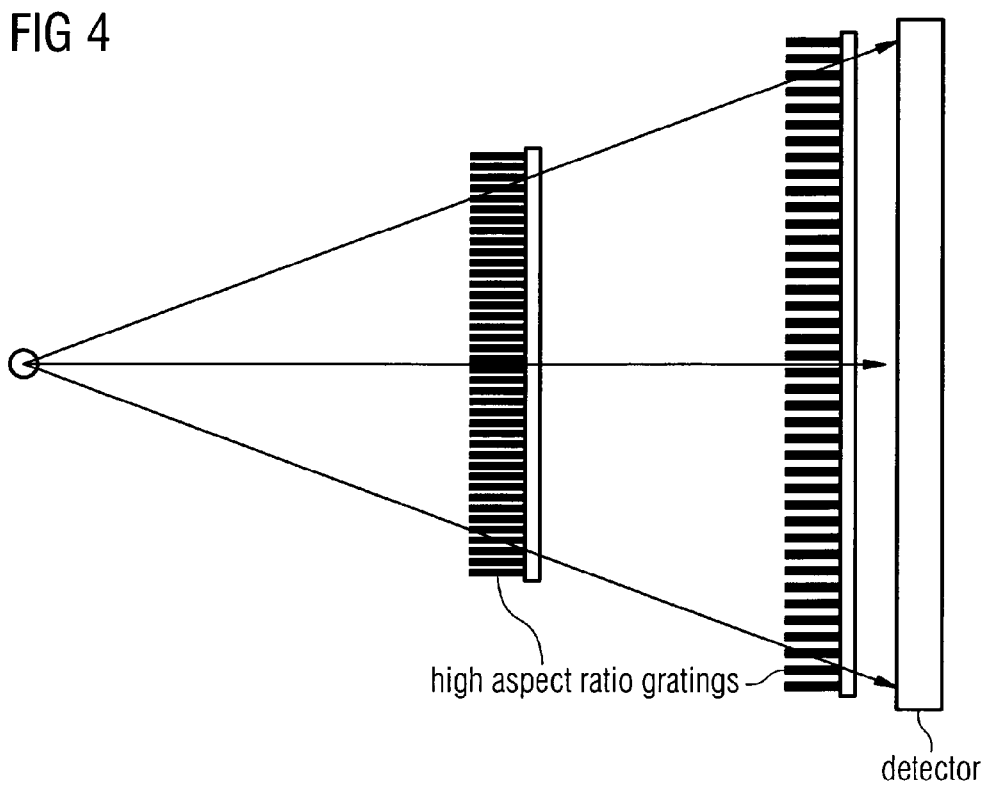
FIG. 4 illustrates exemplarily the problem of high aspect ratio gratings in combination with divergent beams.
Figure 5:
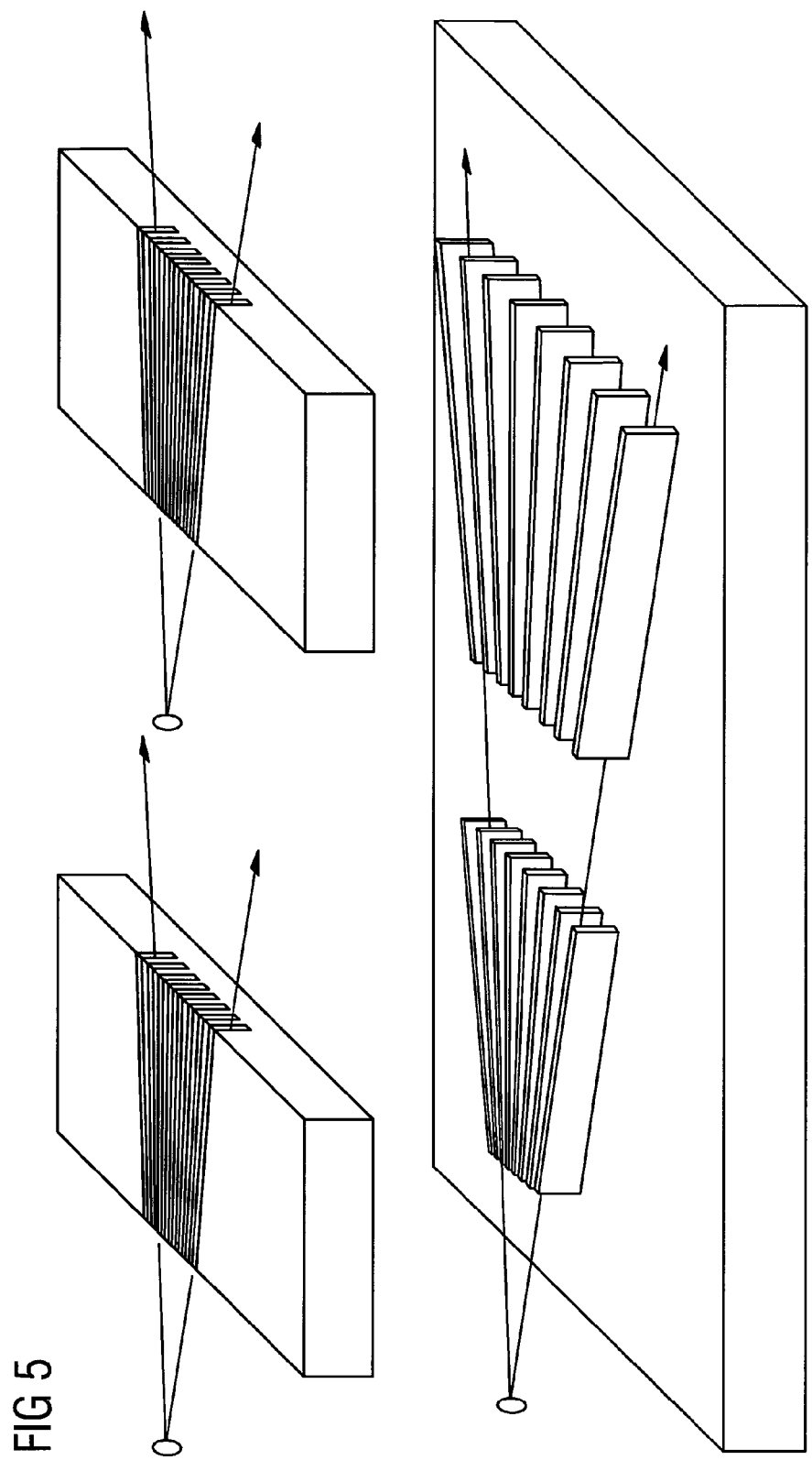
FIG. 5 gives examples of grating structures fabricated using planar technologies: by patterning of a substrate or a substrate layer (top left), by filling the substrate structures or substrate layer structures (top right). Planar technology can also be used to combine several gratings on the same substrate, with excellent relative placement accuracy and mechanical stability (below).

1. High aspect ratio gratings.

A novel planar geometry for gratings-based imaging where the X-rays pass through them parallel to the substrate and not perpendicular to it as it has been done so far. The extension of the grating structures along the x-ray path, which determines the phase shift and attenuation that these structures cause to the x-rays is no longer given by the thickness of the structures, but by the length of the structures. Thanks to this new geometry, planar technology can be used and arbitrary aspect ratios can be obtained.

These planar fabrication technologies include (list not exhaustive)

(a) Micro-machining, e.g. cutting of grooves by a dicing saw.

(b) Lithographic techniques, in particular photo lithography, x-ray lithography, or electron beam lithography, used to pattern a resist layer.

(c) Lithographic techniques, in particular photo lithography, x-ray lithography, or electron beam lithography, used to pattern a resist layer, which is then transferred by etching techniques. Here, deep reactive ion etching of silicon is a very suitable technique.

(d) Lithographic techniques, in particular photo lithography, x-ray lithography, or electron beam lithography, used to pattern a resist layer, which is then transferred by a deposition technique. Here, electroplating (e.g. of gold or nickel) into a mold is a very suitable technique.

(e) Replication techniques to produce copies from masters made by the above-mentioned techniques.

The abovementioned planar fabrication techniques can be used in a variety of ways including:

(i) Patterning a substrate or a substrate layer made of an absorbing material (e.g. a heavy metal) to produce absorption grating structures.

(ii) Patterning a substrate or a substrate layer made of a low absorbing material (e.g. silicon or polymer to produce phase grating structures.

(iii) Patterning a substrate or a substrate layer made of a low absorbing material (e.g. silicon or polymer), and to fill the grooves with a high absorbing material (e.g. a heavy metal) to produce absorption grating structures.

(iv) Patterning a substrate or a substrate layer made of a low absorbing material (e.g. silicon or polymer), and to cover the side walls of the grooves with a high absorbing material (e.g. a heavy metal) to produce absorption grating structures.

Structures along the beam direction can be several mm up to cm long. The planar approach can be applied to fabricate G0 (if required), G1, and G2, or part of such a grating set. Both absorption and phase shifting gratings can be produced by the planar approach. Combinations of G0 and G1, or G1 and G2 can be fabricated on a single substrate with excellent relative placement accuracy and mechanical stability. It could also be envisioned to fabricate the line detector on the same substrate as G2 or a on the same substrate as G1 and G2.

The height of the structures limits the height of the fan beam that can be used. Structure heights of tens of microns or even several hundred microns can be obtained by the planar fabrication techniques. Higher structures can be obtained by stacking two patterned substrates on top of each other, face to face. The mechanical alignment could be done by lithographically defined notches and grooves, designed to make the two substrates snap into each other with the right relative position.

2. Arbitrary shape of the grating geometry—Increased visibility and sensitivity.

According to the aforementioned fabrication approach and illumination scheme it results that the grating structures can be designed and realized following any arbitrary geometry. In particular, this allows matching the divergence of the beam emerging from a conventional X-ray source, resulting in:

i.) increased visibility up to very large field of views ii.) increased sensitivity over the whole field of view 3. Integrated phase stepping Given the planar geometry we suggest different grating designs that can be used to perform phase stepping without the need of physically moving the gratings.

In particular:

a. G1 and G2 can be positioned (either on the same wafer directly during the lithographical process or mechanically if G1 and G2 are on two different supports) in such a manner that the phase relation between G1 and G2 corresponds exactly to the value for which the intensity curve can be expanded by a first order Taylor series according to the "single step" approach.

b. A set of n phase steps can be obtained by using n sets of planar grating and n line detectors, analogous to FIG. 3. By aligning each of the n sets with a different phase-stepping position, the object will be scanned in n phase-step positions without moving any mechanical parts (besides the object). The relative alignment can be achieved by stacking n gratings on top of each other, see FIG. 6. The mechanical alignment could be done by lithographically defined notches and grooves, designed to make the two substrates snap into each other with the right relative position.

The invention claimed is:

1. An X-ray arrangement for obtaining quantitative X-ray images from a sample, comprising:

a) an X-ray source;

b) a set of at least two gratings;

c) a position-sensitive detector with spatially modulated detection sensitivity having a plurality of individual pixels;

d) a recorder connected to said detector for recording images of said detector;

e) evaluation means for evaluating respective intensities for each pixel in a series of images in order to identify a characteristic of the object for each individual pixel as one or more of an absorption-dominated pixel or a differential phase contrast dominated pixel or an x-ray scattering dominated pixel;

f) wherein the series of images is collected by continuously or stepwise rotating from 0 to $\pi$ or $2\pi$ either the sample or the X-ray source relative to the sample;

g) said set of gratings, or part of said gratings being manufactured with planar geometry where the X-rays pass through said gratings parallel to the substrate;

h) said grating structures extending along an x-ray path which determines the phase shift and attenuation that said grating structures cause to the x-rays, not being given by the thickness of said structures, but by a length of said grating structures; and i) wherein a combination of said grating structures of said set of gratings are fabricated on a single substrate.

2. The arrangement according to claim 1, configured to be operated either in a "near field regime" or in a "Talbot-regime."

3. The arrangement according to claim 1, wherein at least one of said gratings is a line grating forming an absorption grating or a phase grating.

4. The arrangement according to claim 1, wherein at least one of said gratings is a low absorption grating configured for generating an X-ray phase shift of it or odd multiples thereof.

5. The arrangement according to claim 3, wherein said gratings include a first grating (G1) and a second grating (G2), with the second grating being a line grating having a relatively high X-ray absorption contrast and a period corresponding to a self image of G1, and wherein G2 is placed closely in front of said detector with the lines of G2 parallel to those of G1.

6. The arrangement according to claim 1, wherein:
for near-field-regime operation, a distance between said at least two gratings is chosen within the near-field regime; and
for Talbot-regime operation the distance is chosen according to $$D_{n,sph} = \frac{L \cdot D_n}{L - D_n} = \frac{L \cdot N \cdot p_1^2 / 2\eta^2 \lambda}{L - N \cdot p_1^2 / 2\eta^2 \lambda}$$

where n=1, 3, 5 . . . , and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2} \end{cases}$$

where l=1, 2, 3, $D_n$ is an odd fractional Talbot distance when the parallel X-ray beam is used, while $D_{n,sph}$ is that when a fan or cone X-ray beam is used, L is a distance between the source and a grating G1.

7. The arrangement according to claim 1, wherein said grating structure is manufactured by planar technology.

8. The arrangement according to claim 1, wherein said grating structures are selected from the group consisting of absorption gratings and phase shift gratings and either or both are produced by a planar technology process.

9. The arrangement according to claim 1, wherein said line detector is fabricated on a common substrate with a second grating or on a common substrate with a first grating and a second grating.

10. The arrangement according to claim 1, wherein a geometry of said grating structure is adapted to a divergence of the X-ray beam.

11. The arrangement according to claim 1, wherein a multiplicity of structures obtained with planar fabrication techniques are stacked face-to-face on top of one another.

12. The arrangement according to claim 1, wherein multiple grating structures are stacked on-top of each other with mechanical or optical alignment.

13. The arrangement according to claim 12, wherein multiple grating structures are aligned by way of lithographically defined notches and grooves.

14. The arrangement according to claim 1, which comprises a collimator placed between said source and a first grating (G1) to limit a spatial extent of the illuminating X-rays to a fan beam, and wherein said detector is a line-array detector, and which further comprises a mechanism for rotating the sample, stepwise or continuously, relative to the apparatus, wherein a rotational axis of the rotation is perpendicular to an opening angle of the fan, and said mechanism is enabled to translate the sample, stepwise or continuously, relative to the apparatus along a direction parallel to the rotational axis.

15. The arrangement according to claim 1, which comprises a slit or a series of n slits disposed upstream of the object, in a beam direction, to minimize dose delivery to the object.

16. The arrangement according to claim 15, wherein said slit or series of n slits is integrated in a grating assembly with a first grating or a grating assembly with a second grating.

17. The arrangement according to claim 1, wherein phase stepping is effected by a mechanical shift of one of said gratings with respect to other said gratings.

18. The arrangement according to claim 1, wherein a phase relation between grating structures G1 and G2 corresponds exactly to a value for which an intensity curve can be expanded by a first order Taylor series.

19. An X-ray arrangement for obtaining quantitative X-ray images from a sample, comprising:
a) an X-ray source;
b) a set of at least two gratings;
c) a position-sensitive detector with spatially modulated detection sensitivity having a plurality of individual pixels;
d) a recorder connected to said detector for recording images of said detector;
e) evaluation means for evaluating respective intensities for each pixel in a series of images in order to identify a characteristic of the object for each individual pixel as one or more of an absorption-dominated pixel or a differential phase contrast dominated pixel or an x-ray scattering dominated pixel;
f) wherein the series of images is collected by continuously or stepwise rotating from 0 to π or 2π either the sample or the X-ray source relative to the sample;
g) said set of gratings, or part of said gratings being manufactured with planar geometry where the X-rays pass through said gratings parallel to the substrate;
h) said grating structures extending along the x-ray path which determines the phase shift and attenuation that said grating structures cause to the x-rays being given by a length of said grating structures;
i) wherein phase stepping is effected by a mechanical shift of one of said gratings with respect to other said gratings; and
j) wherein a first grating is stepped and second and third gratings are physically located on a common substrate and a phase relation between the second and third gratings is encoded within the planar structures.

20. An X-ray arrangement for obtaining quantitative X-ray images from a sample, comprising:
a) an X-ray source;
b) a set of at least two gratings;
c) a position-sensitive detector with spatially modulated detection sensitivity having a plurality of individual pixels;
d) a recorder connected to said detector for recording images of said detector;
e) evaluation means for evaluating respective intensities for each pixel in a series of images in order to identify a characteristic of the object for each individual pixel as one or more of an absorption-dominated pixel or a differential phase contrast dominated pixel or an x-ray scattering dominated pixel;
f) wherein the series of images is collected by continuously or stepwise rotating from 0 to π or 2π either the sample or the X-ray source relative to the sample;
g) said set of gratings, or part of said gratings being manufactured with planar geometry where the X-rays pass through said gratings parallel to the substrate;
h) said grating structures extending along the x-ray path which determines the phase shift and attenuation that said grating structures cause to the x-rays is given by a length of said grating structures; and
i) wherein a set of n phase steps is obtained by using n sets of planar grating and n line detectors; each of the n sets being aligned with a different phase-stepping position, and wherein the object is scanned in n phase-step positions without moving any mechanical parts and only the object.

* * * * *